United States Patent [19]

Clark et al.

[11] Patent Number: 5,223,133
[45] Date of Patent: Jun. 29, 1993

[54] MULTI-FILTER ANALYTICAL APPARATUS

[75] Inventors: Phillip Clark, Stoneham; Frederick G. Bargoot, Wellesley; Yolanda Nieuwkerk, Needham; Aldo M. Pitt, Sudbury, all of Mass.

[73] Assignee: Millipore Corporation, Bedford, Mass.

[21] Appl. No.: 795,452

[22] Filed: Nov. 21, 1991

[51] Int. Cl.$^5$ ................................................ B01D 69/00
[52] U.S. Cl. .................................. 210/232; 210/406; 210/321.84
[58] Field of Search ................... 210/232, 323.1, 406, 210/34.75, 34.84; 422/101

[56] References Cited

U.S. PATENT DOCUMENTS 4,948,564 8/1990 Root et al. ........................... 422/101

Primary Examiner—Frank Spear
Attorney, Agent, or Firm—Andrew T. Karnakis; Paul J. Cook

[57] ABSTRACT

A filtration member transfer apparatus is provided for transferring one or a plurality of discrete reaction or isolation zones such as filtration membranes from a sample isolation step to an analytical apparatus. The transfer apparatus includes a template, preferably which is electrically conductive, having holes or depressions of a size, shape and position corresponding to the reaction or isolation zones. An electrically conductive adhesive is exposed in the holes or depressions of the template.

19 Claims, 3 Drawing Sheets

MULTI-FILTER ANALYTICAL APPARATUS

BACKGROUND OF THE INVENTION

This invention relates to a device which permits simultaneous analysis of a plurality of radioactively labeled discrete reaction or isolation zones such as in a plurality of filters. More particularly, this invention relates to a device for transferring a plurality of radioactively labeled samples to an apparatus for analyzing the samples.

Test plates for in vitro analysis which contain a multiplicity of individual wells or reaction chambers are commonly known laboratory tools. Such devices have been employed for a wide variety of purposes and assays as exemplified by U.S. Pat. Nos. 3,694,464; 4,304,865; 4,276,048; 4,427,415; 4,526,690 and Re 30,562. Microporous membrane filters and filtration devices containing such microporous membranes have been especially useful with many of the recently developed cell and tissue culture techniques and assays, particularly those in the field of virology, cell biology, phamacology, immunology and molecular biology, wherein the material of interest is retained by the filter. Typically, a ninety-six well filtration plate is used to conduct multiple assays simultaneously. Often the material of interest is retained on the filter. However, if an analytical instrument used for sample quantification cannot detect samples on the filters situated directly in the plate wells, the filters must be removed from the wells. This is particularly true when using a weak radiation emitter such as tritium because emissions travel such a short distance from their source and in typical detectors, the well height exceeds the emission distance.

It also has been proposed to utilize a die-punch having a flat face which is inserted into the well and through the filter paper bearing the retentate in order to direct the filter paper and retentate from the well into a vial for subsequent testing. This system has major problems. Scintillation fluid is a hazard which generates a large volume of waste which is costly to dispose of. Any cutting or punching tools can cross contaminate samples. Therefore each sample must have its own punch which generates more waste. In addition, many times only a portion of the filter paper circumference is sheared and the filter disc remains attached to the well. Also, the flat face of the punch tends to remove some of the retentate from the filter paper so that the subsequent testing is inaccurate. An alternative system utilizes a hollow tube as a punch to minimize the contact face of the punch and reduce the amount of sample accidently transferred to the punch. In another system, the filter is scored about its circumference in order to facilitate subsequent punching. This system is undesirable since accidental rupturing of the filter along the scoring can occur.

It has been proposed in U.S. Pat. No. 4,639,601 and U.K. Patent Application 2,168,526A to provide an analytical apparatus for counting radioactive emissions from a plurality of samples. The samples are deposited on a sheet such as from a chromatographic or electrophoretic separation step to produce a radiochromatogram or an electrophoretogram. The apparatus utilizes a resolution plate to isolate the samples from each other as well as a reusable metal plate which permits an appropriate level of electrostatic discharge. These plates are undesirable since they are heavy and cumbersome and are prone to contamination which must be removed through extensive washing prior to analyzing the next successive set of samples. In addition, this apparatus is not capable of analyzing samples labeled with tritium and the reusable metal plate produces a path between the sample and the radioactivity detector which is too long to permit accurate emission measurement.

Accordingly, it would be desirable to provide a means for removing retentate and filter from a multi-well filtration plate which assures that the filter will be completely removed from the well without the loss of a portion of the retentate for purposes of subsequent testing. It would be desirable to provide such a means which maintains sample array spacing to prevent sample cross-talk and which can be easily handled for presentation into an available analytical instrument. Furthermore, it would be desirable to provide such a means onto a surface so that it can be utilized directly in an analytical apparatus while eliminating contamination associated with a reusable metal plate. In addition, it would be desirable to provide such a means which permits record keeping on a disposable unit.

SUMMARY OF THE INVENTION

This invention provides a transfer apparatus for simultaneously transferring a plurality of filters having retentate thereon from a multi-well filtration apparatus to an analytical apparatus. The transfer apparatus is provided with means for preventing electrostatic charge build-up during analysis which means comprises an electrically conductive adhesive and a backing for the adhesive which, preferably, also is electrically conductive. The transfer apparatus comprises a template having holes or depressions corresponding to the size, shape and position of the filters on the multi-well filtration apparatus, and an electrically conductive adhesive positioned within the holes or depressions. preferably the template is electrically conductive so that electrostatic charge build-up can be more easily dissipated during analysis in an analytical apparatus. The adhesive can be supported either by the template or by a backing adhered to the template which backing preferably is electrically conductive. The adhesive bond is exposed within the holes or depressions of the template. The transfer apparatus is used subsequent to using a filtration apparatus to deposit a retentate on the multiple filters. The transfer apparatus is contacted with the filters so that the exposed adhesive in each template hole or depression contacts the surfaces positioned opposite the filter surfaces having the retentate. After the adhesive has bonded to the filters, the transfer apparatus is pulled away from the filtration apparatus so that the filters are removed from the filtration apparatus and are bonded to the exposed adhesive on the transfer apparatus. The transfer apparatus then is inserted into a standard analytical instrument capable of analyzing the signal from retentates simultaneously. The transfer apparatus is used for adhesion to one set of filters and need not be cleaned. However, it can be stored for repeated analytical measurement.

DETAILED DESCRIPTION OF SPECIFIC EMBODIMENTS

This invention provides a transfer apparatus for transferring a plurality of membrane filters from a multi-well filtration plate to an analytical apparatus for analyzing retentate on the membrane filters. The transfer apparatus comprises a template having a plurality of holes or depressions having a size, shape and position which corresponds to the size, shape and position of the membrane filters on the multi-well filtration plate. The holes or depressions serve to isolate samples from each other and thereby prevent cross-contamination. An electrically conductive adhesive is positioned within the holes or depressions of the template and is exposed within the holes or depressions. The conductive adhesive is applied directly to an exposed surface within depressions of the template or is applied to a backing sheet which is preferably electrically conductive or other conductive polymer such as a foil or a conductive foam on other conductive polymer which then is adhered to a template having holes.

When the template includes depressions rather than holes, the adhesive is positioned in discrete locations. The adhesive must be electrically conductive so that electrostatic build-up cannot be dissipated through the adhesive layer. In this case, it is necessary that the template also be electrically conductive so that the charge can be dissipated. When the template includes holes rather than depressions, the adhesive layer can be formed as a continuous layer and, since it is conductive, it can be connected to ground during sample analysis so as to dissipate electrostatic charge build-up. However, in any case, it is preferred to utilize an electrically conductive template and electrically conductive backing so as to facilitate dissipation of electrostatic charge build-up.

When the transfer apparatus is contacted with the exposed bottom surface of the membrane filters, the adhesive is bonded to the filters. The filters can be completely removed from the wells by applying a pressure to the transfer apparatus so that the membrane filters are detached from the multi-well filtration apparatus and are adhered to the conductive adhesive. In this manner, since nothing touches the filter surface which bears the retentate, loss of retentate is prevented and the retentates can be analyzed when positioned in an analytical apparatus for radioactivity detection.

Figure 1:
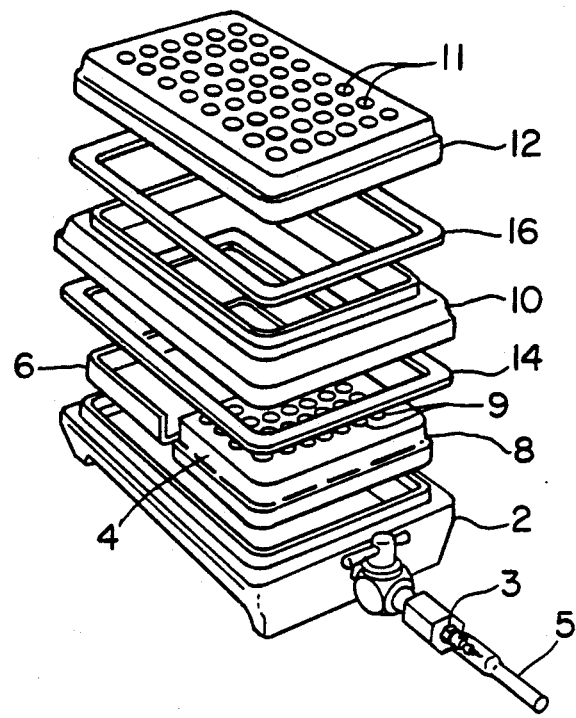
FIG. 1 is an exploded view of a multi-well filtration apparatus useful with the present invention.

Referring to FIG. 1, a vacuum assembly is shown capable of simultaneously processing a plurality of test samples of a size usually up to about 400 microliters each. The vacuum assembly comprises a base 2 which acts as a vacuum chamber and contains hose barb 3 for connection to a regulated external vacuum source through hose 5. Positoned within the base 2 are liquid collection means 4 which includes a collection tray 6 and/or a receiving plate 8 having a plurality of individual chambers 9 for collecting filtrate. The individual chambers 9 are associated each with a single well 11 in multi-well filtration plate 12. A plate support 10 holding the filtration plate 12 above the fluid collection means 4 is separated by gaskets 14 and 16 which form an airtight seal in the presence of a vacuum force exerted through hose 5. It is to be understood that FIG. 1 merely shows a representative multiwell arrangement with which the transfer apparatus of this invention can be utilized. Any conventional multiwell apparatus having a plurality of membrane filters can be utilized with present invention.

Figure 2:
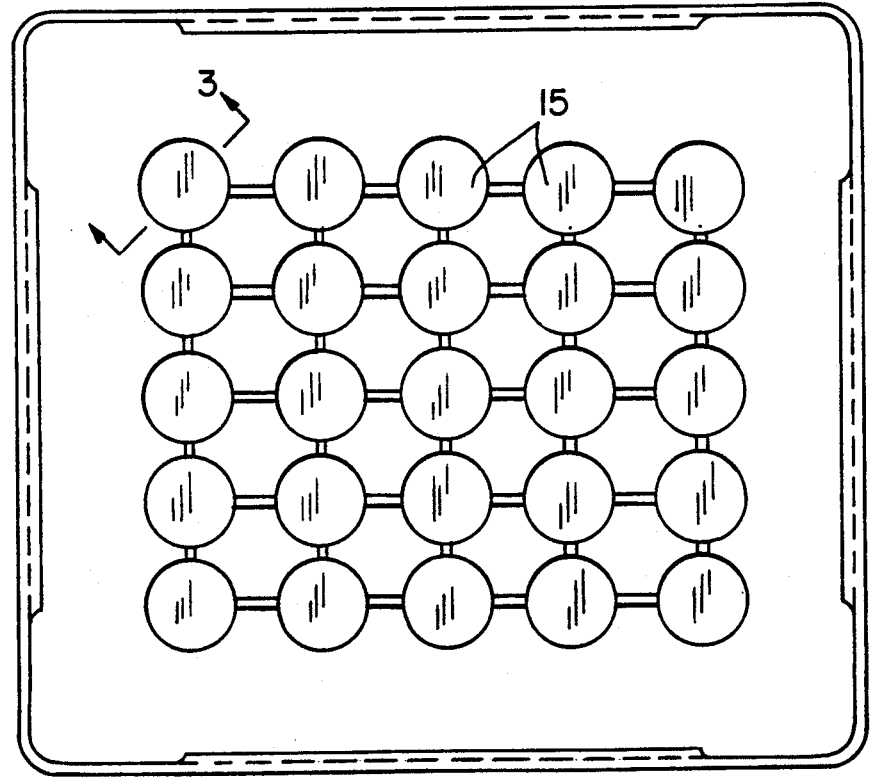
FIG. 2 is a top view of a multi-well filtration plate.
Figure 3:
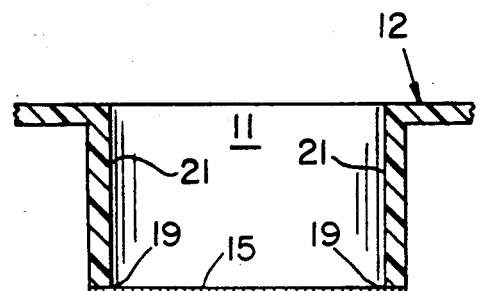
FIG. 3 is a cross sectional view of a well of FIG. 2 taken along line 3—3.

Referring to FIGS. 2 and 3, plate 12 includes a plurality of wells 11 to which are bonded filtration membranes 15. The filtration membranes 15 are bonded to the lower surface 19 of well wall 21. Well 11 extends downwardly to the point such that liquid passing through membrane 15 is directed into a receptacle (not shown). Any conventional bonding method can be utilized to bond membrane 15 to plate 12 so long as the filtration membrane can be subsequently detached in accordance with this invention. The filtration membranes can be bonded, for example, by the steps of heat sealing a membrane sheet to the bottom surfaces of the wells 11 and then cutting the membrane sheet into the desired shapes such as by laser. Representative suitable micro-porous membranes include nitrocellulose, cellulose acetate, polycarbonate, polyamide, polypropylene and polyvinylidene fluoride microporous membranes. Alternatively, the membrane can comprise an ultrafiltration membrane, which membranes are useful for retaining molecules as small as about 100 daltons and generally molecules as large as about 2,000,000 daltons. Examples of such ultrafiltration membranes include polysulfone, polyvinylidene fluoride or cellulose or the like. Also, the membrane can be comprised of depth filter media such as paper glass fibers or polymeric nonwoven fibers an polymeric nonwovens. In addition, the filter membrane can be formed as a laminate structure comprising a membrane bonded to a woven or non-woven substrate.

Figure 4:
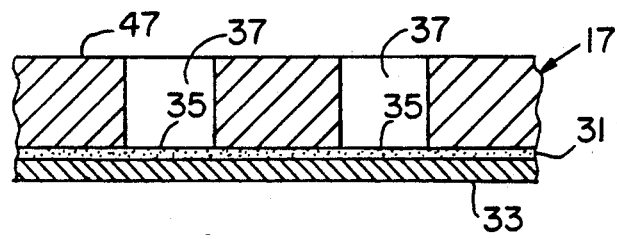
FIG. 4 is a cross-sectional view of the transfer apparatus of this invention.
Figure 6:
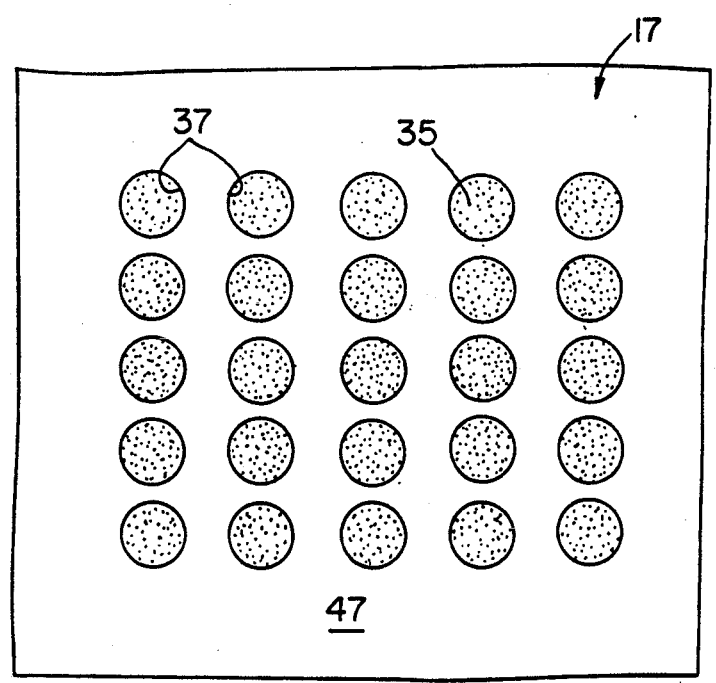
FIG. 6 is a top view of the transfer apparatus of FIG. 4.

Referring to FIGS. 4 and 6, the transfer apparatus of this invention includes an electrically conductive template 17 such as a carbon-filled or metal particle-filled polymer composition such as polyacrylonitrile-butadiene-styrene (ABS), polyether, polystyrene or the like. The template 17 has a thickness which permits the retentate to be analyzed without contamination or cross-talk between samples. For example, when the retentate is analyzed for the presence of tritium, the template thickness should be between about 0.005 and 0.250, preferably between about 0.015 and 0.020 inch. When isotopes having higher radiation energies than tritium are utilized, such as $^{125}I$, $^{14}C$, $^{35}S$, $^{32}P$ or $^{99m}Tc$, typical template thicknesses are between about 0.02 and 0.75, preferably between about 0.1 to 0.25 inch. The adhesive 31 must be electrically conductive so that electrostatic charges in the template can be dissipated so as to avoid interference with the retentate sample analyses. The adhesive sections 35 one exposed within holes 37 of template 17 for subsequent contact with filtration membranes as described herein. Suitable adhesives include pressure sensitive adhesives, heat activatable adhesives, ultraviolet light activated adhesives or the like. Thus, the adhesive is tacky or is rendered tacky such as with heat or light. The conductive backing 33 coated with the adhesive can comprise a metal foil such as aluminum foil, or the like or a conductive foam material.

Figure 5:
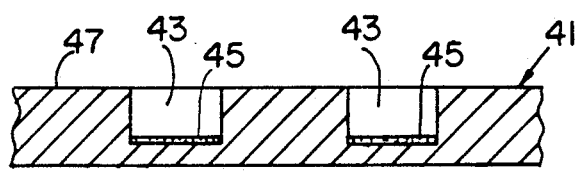
FIG. 5 is a cross-sectional view of an alternative embodiment of the transfer apparatus of this invention.

Referring to FIG. 5, the electrically conductive template 41 is provided with depressions 43 rather than through-holes. Thus, exposed conductive adhesive 45 is positioned on a template surface rather than on a conductive backing as shown in FIG. 4. With the template structures of FIGS. 4 and 5, the template thickness defined as the distance between the top surface 47 of the template and the exposed adhesive 35 or 45 varies depending upon the radiolabel of use as described above. After filter membrane deposition on the exposed adhesive 35 or 45, the template is inserted into an apparatus for detecting radiolabels such as is disclosed in U.S. Pat. No. 4,639,601 and U.K. Patent Application 2,168,526A which are incorporated herein by reference.

Figure 7:
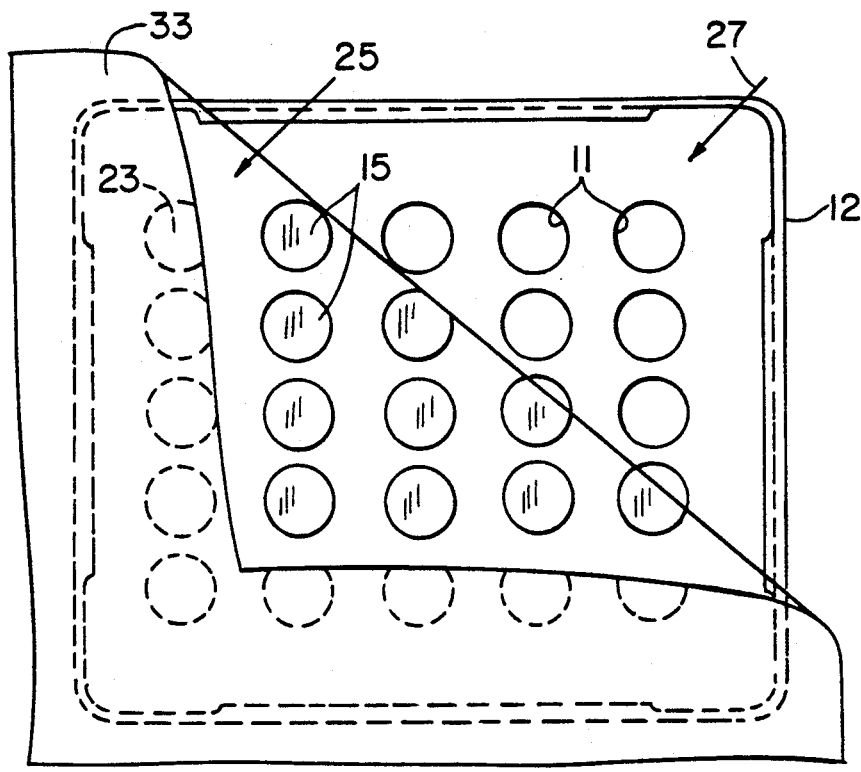
FIG. 7 is a top view illustrating the use of the transfer apparatus of this invention.

Referring to FIG. 7, after filtration has been completed so that retentate is positioned on the membrane surfaces within wells 11, the transfer apparatus 25 is applied to the retentate-free bottom surface 23 of the membrane 15 under pressure so that the filter membranes 15 are adhered to adhesive 31. The transfer apparatus 25 then is pulled in the direction of arrow 27. As shown in FIG. 6, the membranes 15 are adhered to the transfer apparatus and the individual retentates thereon are exposed for analysis.

Figure 8:
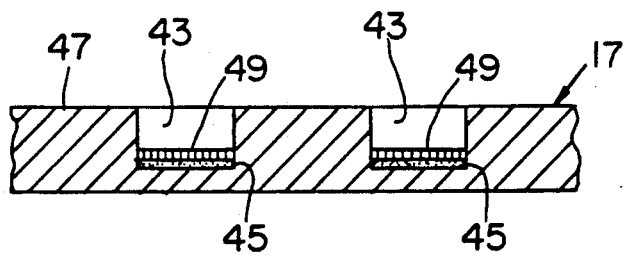
FIG. 8 is a cross-sectional view of an alternative apparatus of this invention including a membrane filter layer.

Referring to FIG. 8, an apparatus of this invention is shown by a filter layer 49 positioned on an electrically conductive adhesive 45. The adhesive 45 is positioned in depression 43 of electrically conductive template 17. This apparatus is useful with radiolabeled samples which need not be filtered. The sample is applied to the filter layer 49 such as by pipetting. The filter layer 49 provides a porous medium for retaining a sample within the depression 43. Similarly, the apparatus of FIGS. 4 and 6 can be modified to include a filter membrane layer 49.

EXAMPLE I

The following example illustrates the present invention and is not intended to limit the same.

Various filtration membrane apparatus and prototypes of filtration apparatus were tested for reproducibility variability (as defined by percent coefficient variation) over time and for count efficiency in analyzing DNA samples containing tritium labeled thymidine. The apparatus were tested in the presence of or in the absence of a membrane. A known concentration of DNA was pipetted into holes of an electrically conductive or nonconductive template having a conductive adhesive, a nonconductive adhesive or no adhesive. Electrically conductive or non-conductive substrates adhered to the template were used in the test. The filtration transfer apparatus tested comprised a template with 96 holes 0.020 inch in height, a substrate adhered to the template and an intervening adhesive in order to adhere the substrate to the template the adhesive was either exposed in the holes or not exposed in the holes. The function of the filtration transfer apparatus was tested in the Mark II detector made by AMBIS Systems, Inc., San Diego, California which is capable of detecting and quantifying the ionizing effect on a gas induced from radiation from a sample.

In the table below, CV is the coefficient of variation defined as the standard deviation (SD) divided by the mean measurement times 100. Efficiency is defined as the counts per minute (CPM) detected by the apparatus divided by the disintegration per minute of the radioactivity in the sample. One millicurie is equal to $2.2 \times 10^6$ disintegrations per minute (dpm).

The results are shown in Table I.

TABLE I

| Sample | Template | Adhesive | Backing | 2 Min % CV | 2 Min % Eff. | 5 Min % CV | 5 Min % Eff. | 15 Min % CV | 15 Min % Eff. |
|---|---|---|---|---|---|---|---|---|---|
| 1 | Non. | Non. | Non. | 123 | 0.07 | 157 | 0.1 | 214 | 0.2 |
| 2 | Con. | 0 | Con. Al | 4.5 | 26.9 | 13.3 | 27.6 | 4.1 | 27.8 |
| 3 | Non. | Con. | Con. Foam | 16.9 | 1.9 | 17.4 | 2.0 | 17.5 | 2.1 |
| 4 | Non. | Con. | Con. Al | 46.6 | 1.8 | 47.8 | 1.8 | 49.5 | 1.8 |
| 5 | Con. | Con. | Con. Al | 16.9 | 3.2 | 17.1 | 3.3 | 17.3 | 3.3 |
| 6 | Non. | Con. | Con. Al Membrane | 24.8 | 1.3 | 25.8 | 1.2 | 25.8 | 1.1 |
| 7 | Con. | Con. | Con. Al Membrane | 15.6 | 3.4 | 15.7 | 3.5 | 15.7 | 3.5 |

In Table I, "Non" is nonconducting, "Con" is conducting and "Al" is aluminium foil (also a conducting material). Samples 6 and 7 included a 0.45 um polyvinylidenedifluoride Durapore HVPP membrane available from Millipore Corporation, Bedford, MA adhered directly to the adhesive. The better samples are those with the lower % CV and the higher % Eff. The lowest performing sample is sample 1. The highest performing sample is sample 2 but it included no adhesive with which to bind the membrane and therefore is not useful. The remaining samples are embodiments of this invention wherein the best performing samples are those with a conductive template, backing and adhesive.

We claim:

1. A filtration membrane transfer apparatus for removing a plurality of discrete filtration membranes from a multi-well filtration apparatus which comprises:
   an electrically conductive template having holes of a size, shape and position as said plurality of discrete filtration membranes,
   an electrically conductive substrate coated on one surface with an adhesive adhered to one surface of said electrically conductive substrate,
   said adhesive being electrically conductive and being exposed in said holes.

2. The apparatus of claim 1 wherein said substrate is a foam.

3. The apparatus of claim 1 wherein said substrate is a metal foil.

4. A filtration membrane transfer apparatus for removing a plurality of discrete filtration membranes from a multi-well filtration apparatus which comprises,
   an electrically conductive template having depressions of size, shape and position as said plurality of discrete filtration membranes,
   and an electrically conductive adhesive coated on a bottom surface of said depressions.

5. The apparatus of any one of claims 1, 2 or 3 wherein said holes have a depth between about 0.005 and 0.250 inch.

6. The apparatus of any one of claims 1, 2 or 3 wherein said holes have a depth between about 0.02 and 0.75 inch.

7. The apparatus of claim 4 wherein said depressions have a depth between about 0.005 and 0.250 inch.

8. The apparatus of claim 4 wherein said depressions have a depth between about 0.02 and 0.75 inch.

9. The apparatus of anyone of claims 1, 2, or 3 being a filter layer adhered to said adhesive and said holes have a depth between about 0.005 and 0.250 inch.

10. The apparatus of anyone of claims 1, 2, or 3 being a filter layer adhered to said adhesive and said holes have a depth between about 0.02 and 0.75 inch.

11. The apparatus of claim 4 having a filter layer adhered to said adhesive and said depressions have a depth between about 0.005 and 0.250 inch.

12. The apparatus of claim 4 having a filter layer adhered to said adhesive and said depressions have a depth between about 0.02 and 0.75 inch.

13. An apparatus for housing a plurality of samples to be analyzed for radioactivity which comprises:

a template having a plurality of holes, an electrically conductive substrate coated on one surface with an electrically conductive adhesive and adhered to one surface of said template, and a filter adhered to said adhesive in said holes.

14. The apparatus of claim 13 wherein said holes have a depth between about 0.005 and 0.250 inch.

15. The apparatus of claim 13 wherein said holes have a depth between about 0.02 and 0.75 inch.

16. The apparatus of claim 13 wherein said template is electrically conductive.

17. An apparatus for housing a plurality of samples to be analyzed for radioactivity which comprises:

an electrically conductive template having a plurality of depressions with a bottom surface, an electrically conductive adhesive adhered to said bottom surface in said depressions, and a filter adhered to said adhesive in said depressions.

18. The apparatus of claim 17 wherein said depressions have a depth between about 0.005 and 0.250 inch.

19. The apparatus of claim 17 wherein said depressions have a depth between about 0.02 and 0.75 inch.

* * * * *